US010591435B2

(12) United States Patent
Conte et al.

(10) Patent No.: US 10,591,435 B2
(45) Date of Patent: Mar. 17, 2020

(54) ELECTROPOLYMERIZATION ONTO FLEXIBLE SUBSTRATES FOR ELECTRONIC APPLICATIONS

(71) Applicant: Cornell University, Ithaca, NY (US)

(72) Inventors: Sean Conte, Gaithersburg, MD (US); Gabriel G. Rodriguez-Calero, Willseyville, NY (US); Cen Tan, Fremont, CA (US); Kenneth Hernandez-Burgos, Ithaca, NY (US); Hector D. Abruna, Ithaca, NY (US); Nicole Ritzert, Renfrew, PA (US); Daniel C. Ralph, Ithaca, NY (US); Wan Li, Kensington, CA (US)

(73) Assignee: Cornell University, Ithaca, NY (US)

( * ) Notice: Subject to any disclaimer, the term of this patent is extended or adjusted under 35 U.S.C. 154(b) by 182 days.

(21) Appl. No.: 15/301,085

(22) PCT Filed: Apr. 3, 2015

(86) PCT No.: PCT/US2015/024276
§ 371 (c)(1),
(2) Date: Sep. 30, 2016

(87) PCT Pub. No.: WO2015/153989
PCT Pub. Date: Oct. 8, 2015

(65) Prior Publication Data
US 2017/0023513 A1     Jan. 26, 2017

Related U.S. Application Data

(60) Provisional application No. 61/974,757, filed on Apr. 3, 2014.

(51) Int. Cl.
G01N 27/30      (2006.01)
H01L 31/0224   (2006.01)
(Continued)

(52) U.S. Cl.
CPC ...... G01N 27/302 (2013.01); B01L 3/502707 (2013.01); C25D 9/02 (2013.01);
(Continued)

(58) Field of Classification Search
CPC .............................. H01L 31/0224–31/022491
See application file for complete search history.

(56) References Cited

U.S. PATENT DOCUMENTS

2011/0183180 A1    7/2011   Yu et al.
2012/0164433 A1    6/2012   Advincula
(Continued)

FOREIGN PATENT DOCUMENTS

WO    2012/064285 A1    5/2012
WO    2013/066474 A2    5/2013
WO    2014/011239 A2    1/2014

OTHER PUBLICATIONS

Davies et al., J. of Phys. Chem. C, vol. 115, pp. 17612-17620 (Year: 2011).*

Primary Examiner — Ramsey Zacharia
(74) Attorney, Agent, or Firm — Hodgson Russ LLP (57) ABSTRACT

Electropolymerized polymer or copolymer films on a conducting substrate (e.g., graphene) and methods of making such films. The films may be part of multilayer structures. The films can be formed by anodic or cathodic electropolymerization of monomers. The films and structures (e.g., multilayer structures) can be used in devices such as, for example, electrochromic devices, electrical-energy storage devices, photo-voltaic devices, field-effect transistor devices, electrical devices, electronic devices, energy-generation devices, and microfluidic devices.

22 Claims, 8 Drawing Sheets

Flexible Transparent Polymer (e.g. PET)

Graphene

Electropolymerizable Material

Electrolyte

Graphene

Flexible Transparent Polymer (e.g. PET)

(51) Int. Cl.

| | | |
|---|---|---|
| *H01G 9/042* | (2006.01) | |
| *H01G 11/32* | (2013.01) | |
| *H01G 9/20* | (2006.01) | |
| *H01G 11/38* | (2013.01) | |
| *H01G 11/48* | (2013.01) | |
| *B01L 3/00* | (2006.01) | |
| *C25D 9/02* | (2006.01) | |
| *G01N 27/414* | (2006.01) | |
| *G01N 27/416* | (2006.01) | |
| *H01G 11/36* | (2013.01) | |
| *G02F 1/155* | (2006.01) | |
| *H01M 4/04* | (2006.01) | |
| *H01M 4/137* | (2010.01) | |
| *H01M 4/1399* | (2010.01) | |
| *H01M 4/60* | (2006.01) | |
| *H01M 4/66* | (2006.01) | |
| *H01L 51/00* | (2006.01) | |
| *H01G 9/035* | (2006.01) | |
| *H01G 9/145* | (2006.01) | |
| *H01G 11/58* | (2013.01) | |
| *H01M 6/02* | (2006.01) | |
| *H01M 10/02* | (2006.01) | |

(52) U.S. Cl.
CPC ..... *G01N 27/4146* (2013.01); *G01N 27/4167* (2013.01); *H01G 9/2059* (2013.01); *H01G 11/36* (2013.01); *H01G 11/38* (2013.01); *H01G 11/48* (2013.01); *H01L 31/022466* (2013.01); B01L 2200/12 (2013.01); B01L 2300/0645 (2013.01); B01L 2300/0887 (2013.01); G02F 1/155 (2013.01); H01G 9/035 (2013.01); H01G 9/042 (2013.01); H01G 9/145 (2013.01); H01G 11/58 (2013.01); H01L 51/0006 (2013.01); H01M 4/0404 (2013.01); H01M 4/0466 (2013.01); H01M 4/137 (2013.01); H01M 4/1399 (2013.01); H01M 4/608 (2013.01); H01M 4/663 (2013.01); H01M 6/02 (2013.01); H01M 10/02 (2013.01); Y02E 10/542 (2013.01); Y02E 60/13 (2013.01)

(56) References Cited

U.S. PATENT DOCUMENTS

2013/0320302 A1    12/2013   Park et al.
2014/0131761 A1*   5/2014   Kwon ............... H01B 1/04
                                                                                            257/99

* cited by examiner

1. Fabricate source drain leads

2. Transfer graphene (with PMMA)

3. Pattern the graphene a. photolithography b. Oxygen plasma

4. Remove the Photoresist and PMMA

ELECTROPOLYMERIZATION ONTO FLEXIBLE SUBSTRATES FOR ELECTRONIC APPLICATIONS

CROSS-REFERENCE TO RELATED APPLICATIONS

This application claims priority to U.S. provisional patent application No. 61/974,757, filed Apr. 3, 2014, the disclosure of which is incorporated herein by reference.

STATEMENT REGARDING FEDERALLY SPONSORED RESEARCH

This invention was made with government support under contract nos. 0847926, DMR-1120296, and ECCS-0335765 awarded by the National Science Foundation. The government has certain rights in the invention.

FIELD OF THE DISCLOSURE

The present disclosure generally relates to electropolymerized materials and structures/devices comprising electropolymerized materials. More particularly, the present disclosure relates to electropolymerization on conducting substrates.

BACKGROUND OF THE DISCLOSURE

Graphene has been proposed as an alternative to commonly used materials such as tin-doped indium oxide (ITO) due to graphene's extraordinary electrical, physical, and mechanical properties. Graphene (as well as any conducting flexible substrate) can be employed as the transparent electrode, instead of the more commonly used indium tin oxide (ITO), due to its extraordinary electrical, physical, and mechanical properties. In addition, the abundance of carbon makes the use of graphene in large-scale applications, such as smart windows, more affordable, than the limited and expensive ITO alternative.

During the past decade since it was isolated through simple exfoliation, graphene has demonstrated interesting optical, mechanical, and electronic properties. Graphene has also found use in electrochemical systems, from sensing devices to fundamental studies of its charge transfer properties. Large area, single layer graphene is interesting because unlike graphene flakes, it can be used as the sole electrode material, removing the need for a conductive substrate and thus allowing for measurements on graphene without complications from the underlying substrate. Single layer graphene also offers the opportunity for simultaneously probing two interfaces in proximity. Recent debate has focused on any differences in charge transfer processes the edges and basal planes of graphene and the effect of impurities introduced during growth and processing on the catalytic properties of graphene.

BRIEF SUMMARY OF THE DISCLOSURE

Figure 1:
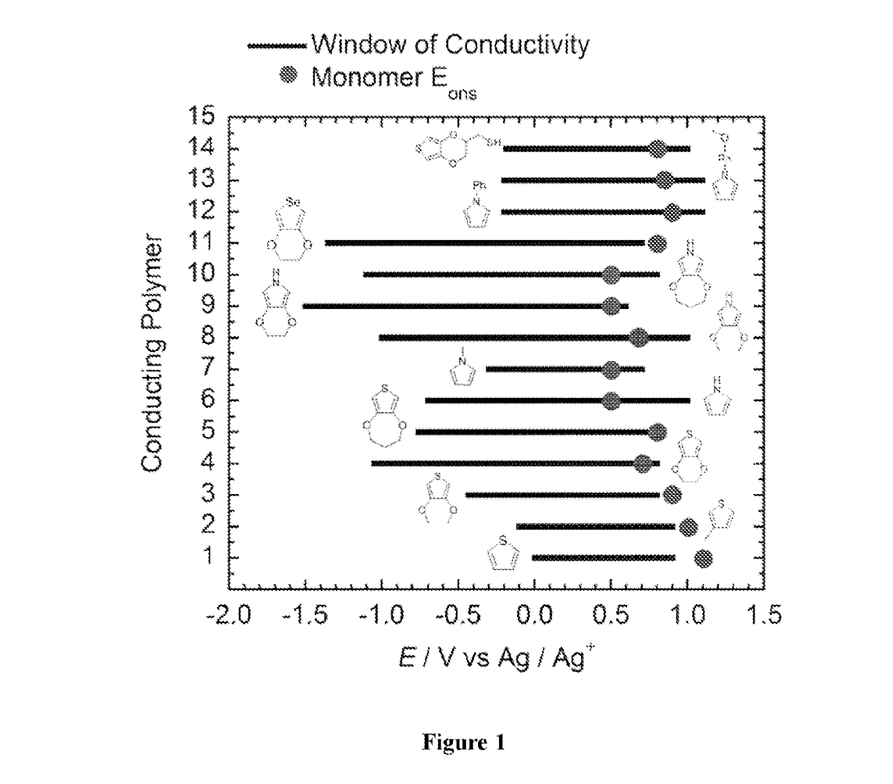
FIG. 1. Window of conductivity (heavy lines) and monomer oxidation onset potential (dots) plot for the indicated monomers.

The electropolymerization of organic or inorganic compounds on large area graphene (or any conducting flexible substrate) electrodes is disclosed herein. FIG. 1 depicts the monomer oxidation onset potentials and the window of conductivity of the corresponding polymer for broad families of materials. The dots indicate the location of the onset potential for anodic oxidation of the monomer precursors, and the heavy line represents the electrochemical potential range over which the polymer is p-doped and electronically conductive. The onset of electrochemical oxidation of the electropolymerizable monomers, (shown as the dots), reflects the minimum applied potential required to electropolymerize the desired monomer onto the graphene (or any conducting flexible substrate) surface. The window of conductivity and the onset of conductivity correlate with the HOMO (Highest Occupied Molecular Orbital) level of the polymer and the electronic structure of the polymer.

These electropolymerization processes can be used to demonstrate the use of graphene (or any conducting flexible substrate) in applications that require transparent electrode/electropolymerized materials, including but not limited to electrochromic displays, electrochemical energy storage, organic light emitting diodes, flexible electronics, and photo-voltaic devices. Moreover, the electrochemical methods employed provide advantages in terms of sample preparation, cost and processability, especially when compared to chemical or physical deposition techniques. Furthermore, by using electropolymerization methodologies like potentiodynamic, galvanostatic, and potentiostatic methodologies; one can control the properties of the deposited film including, thickness, electronic structure, chemical structure, and morphology.

Figure 2:
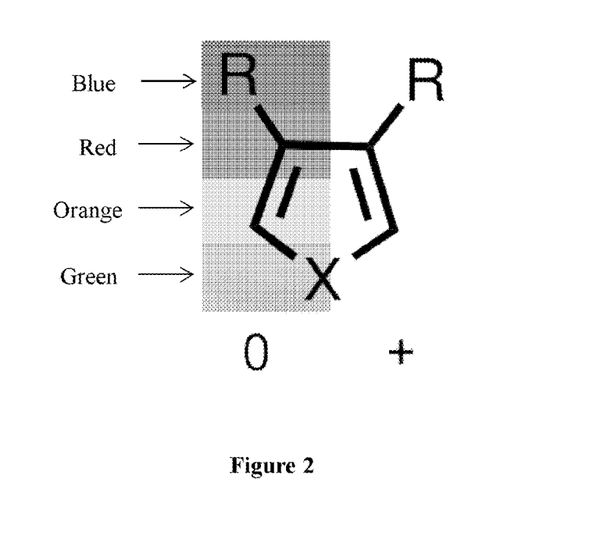
FIG. 2. Representative structure of electropolymerizable material and color change schematic.

The application space in which the following materials are used in, and the methodologies employed for the preparation and synthesis of said materials, are important in applications such as electrochromic devices, electrical energy storage, flexible electronics, flexible displays, light emitting diodes, sensors, and photo-voltaic devices. An example of the possible color changes occurring in electrochromic applications can be observed in FIG. 2.

BRIEF DESCRIPTION OF THE FIGURES

FIG. 4(a). 0 minutes, FIG. 4(b). 1 minute, FIG. 4(c). 2 minutes and FIG. 4(d). 3 minutes of electrochemical cycling.

FIGS. 8(a)-8(b). Example of graphene FET fabrication.

FIGS. 9(a)-9(d). Example of solution-gated graphene FET fabrication.

FIGS. 10(a)-10(c). Example of solution-based ECL with TPrA.

FIGS. 11(a)-11(c).

FIGS. 12(a)-12(d).

FIGS. 13(a)-13(b).

FIGS. 15(a)-15(d). pH sensitivity of examples of solution-gated graphene FETs.

DETAILED DESCRIPTION OF THE DISCLOSURE

The present disclosure provides structures (e.g., multilayer structures) with one or more electropolymerized layers. Also provided are methods of making the structures (e.g., multilayer structures) and uses of the structures.

Electropolymerizable materials (e.g., conducting polymers, vinyl polymers, organosulfur compounds, etc.) are of great interest in electrochromic displays, electrochemical energy storage, organic light emitting diodes, flexible electronics, and photo-voltaic devices because of their long-term stability, low oxidation potential, high contrast ratio, fast charge/discharge rates, tunable electronic structure, and fast switching times (FIG. 1). Methodologies for electropolymerizing organic and inorganic compounds onto graphene (e.g., large area graphene) (and, in principle any conducting flexible substrate) electrodes through the use of electrochemical techniques (including but not limited to: cyclic voltammetry, chronoamperometry and galvanostatic methods) were developed. These electropolymerization process provides advantages in terms of sample preparation, cost and processability, in particular when compared to other chemical and physical deposition methods. The use of electrochemical techniques provides control over materials properties such as thickness, electronic structure, chemical structure and morphology by changing the deposition parameters/conditions.

The combination of graphene (or any conducting flexible substrate) with the electropolymerized materials, as well as the methodologies by which they are prepared, are important and valuable in various applications including electrochromic devices, electrical energy storage, flexible electronics, flexible displays, light emitting diodes, sensors, and photo-voltaic devices. Processes and methodologies through which the assembly of composites onto flexible substrates were developed. In addition, the new methodologies allow previously unachievable combinations, by other deposition methods such as spin coating, of materials, (e.g., poly-3,4-ethylenedioxythiophene (PEDOT)/graphene composites).

In an aspect, the present disclosure provides structures (e.g., multilayer structures). The structures comprise an electropolymerized layer disposed on (i.e., in contact with) a conducting substrate. For example, the conducting substrate is a flexible substrate such as a graphene layer.

In various embodiments, a structure comprises a conducting substrate (e.g., a substrate comprising a first graphene layer (e.g., a single layer of graphene or multiple layers of graphene) disposed on at least a portion, substantially all, or all of a surface of a substrate) and a first electropolymerized polymer layer disposed on at least a portion, substantially all, or all of the conducting substrate (e.g., the first graphene layer). The structure (e.g., a multilayer structure) may have two or more (i.e., multiple) graphene layers. The structure (e.g., a multilayer structure) may have two or more (i.e., multiple) electropolymerized layers.

The structure (e.g., a multilayer structure) structure has one or more conducting substrates. The conducting substrates are conducting or semiconducting. The conducting substrates may be planar or non-planar. The conducting substrate can comprise layers of different materials (e.g., one or more layers of conducting materials, one or more layers of non-conducting materials, and/or one or more layers of semiconducting materials). The conducting substrate can be made of a conducting or semiconducting material or a non-conducting material that has a material that is conducting or semiconducting (e.g., an exposed layer of a conducting or semiconducting material on a substrate). For example, the conducting substrates are formed from materials such as metals, metal oxides, metal nitrides, semiconducting materials, glasses (e.g., coated glasses), and graphene.

One or more of the conducting substrates present in the structure (e.g., a multilayer structure) may be flexible substrates. The flexible substrate can be formed from any common transparent plastic/polymer or copolymer. Examples of flexible substrate materials include poly(ethylene terephthalate) (PET), poly-3,4-ethylenedioxythiophene-polystryrenesulfonate, polyethylene, polypropylene, polystryrene, and copolymers thereof.

The electrodeposited material can be disposed on at least a portion, substantially all, or all of a graphene layer. The graphene layer is conducting. The graphene can be a single layer of graphene or multiple graphene layers. For example, the graphene layer comprises 2 to 10 individual graphene layers. The graphene can be planar or non-planar. The graphene layer may be continuous or discontinuous (e.g., the layer may have one or more areas without graphene). For example, the graphene layer has an area of 0.01 cm$^2$ to 10 m$^2$. In certain instances, a graphene layer is referred to herein as large area graphene. By large area graphene, it is meant that the graphene can be handled and processed using the methods described herein. In another example, the graphene layer is in roll form or a flexible substrate comprising a graphene layer in roll form. The graphene may be disposed on a flexible material (e.g., a non-conducting material) to provide a conducting flexible substrate. The graphene layer can be formed by methods known in the art.

The graphene layer can be a modified graphene layer. The graphene can be modified with, for example, 3,4-DHB (3,4-dihydrobenzene). In an embodiment, the graphene is modified with a film of 3,4-DHB (3,4-dihydrobenzene).

The electropolymerized layer can be formed by the methods of the present disclosure. In an embodiment, the electropolymerized layer is formed by a method of the present disclosure. The electropolymerized layer can be distinguished from polymer layers formed by other methods. The electropolymerized layer grows directly on the conducting substrate (e.g., a graphene layer). The electropolymerized layer is not formed from pre-formed polymers (i.e., is not formed by casting pre-formed polymers). The electropolymerized layer is not formed by casting. The electropolymerized layer has desirable characteristics. The electropolymerized layer can have lower contact resistance than polymer layers formed from the same monomer(s) and having the same characteristics, such as layer thickness. In various embodiments, the electropolymerized layer has 10 times or less, 5 times or less, or 2 times or less contact resistance than a polymer layer formed from the same monomer(s) and having the same film thickness.

The electropolymerized layer can be conducting, non-conducting, or semiconducting. The electropolymerized layer can be an organic electropolymerized layer or an inorganic polymerized layer. The electropolymerized layer is disposed on at least a portion substantially all, or all of the substrate (e.g., graphene layer). The structure comprises one or more electropolymerized layers. The electropolymerized layers are, independently, homopolymers or copolymers. For example, the electropolymerized layer(s) has/have a thickness of mm to 1 mm, including all integer nm values and ranges therebetween. In an embodiment, the electropolymerized layer has a thickness of 10 nm to 1 micron. The electropolymerized layer can be formed as described herein. The electropolymerized layer conformally covers at least a portion, substantially all, or all of the graphene layer. In an embodiment, the electropolymerized layer is a polythiophene, polythiophene derivative, polypyrrole, polypyrrole derivatives, polyfuran, polyfuran derivatives, polyaniline, polyaniline derivative, polyphenylenediamine, polyphenylenediamine derivatives, polyvinyl derivatives (e.g., polymers of vinyl-substituted bipyridine metal salts such as poly[tris-(vinyl bipyridine)M], where M is a metal such as, for example, ruthenium, osmium, iron, cobalt, nickel, or rhenium), or a copolymer thereof.

Examples of electropolymerized layers include poly(3,4-(1-thiomethyl)ethylenedioxythiophene (poly(2,3-dihydrothieno[3,4-b][1,4]dioxin-3-ylmethanethiol)); poly(N-methoxyphenylpyrrole) (e.g., poly(1-(4-methoxyphenyl)-pyrrole); poly(N-phenylpyrrole); poly(3,4-ethylenedioxyselenophene); poly(3,4-propylenedioxypyrrole); poly(3,4-ethylenedioxypyrrole); poly(3,4-dimethoxypyrrole); poly(N-methylpyrrole); polypyrrole; poly(3,4-propylenedioxythiophene); poly(3,4-ethylenedioxythiophene) (PEDOT); poly(3,4-dimethoxythiophene); poly(3-methylthiophene); polythiophene; poly[tris-(4-vinyl-4'-methyl-2,2'-bipyridine)M]$^{2+}$, where M is a metal such as M is a metal such as, for example, ruthenium, osmium, iron, cobalt, nickel, or rhenium), and copolymers thereof.

The structure (e.g., a multilayer structure) may include an electrolyte layer (e.g., a first electrolyte layer) disposed on at least a portion, substantially all, or all of an electropolymerized layer. An electrolyte layer may have a graphene layer disposed on at least a portion, substantially all, or all of the electrolyte layer. Examples of suitable electrolyte materials include polymer electrolytes (e.g., polyethyleneoxide), organic electrolyte solutions (e.g., perchlororate salts in acetonitrile or a carbonate), and aqueous electrolyte solutions (e.g., aqueous sodium chloride or potassium fluoride).

The structure (e.g., a multilayer structure) structure may include one or more flexible transparent polymer layers. These layers, if present, are disposed on at least a portion, substantially all, or all of one or more of the graphene layers present in the structure. Any common transparent plastic/polymer or copolymer can be used as flexible transparent polymer layer. The flexible transparent polymer layers can be deposited by methods known in the art. For example, the layer is deposited by spin coating. Examples of flexible transparent materials include poly(ethylene terephthalate) (PET), poly-3,4-ethylenedioxythiophene-polystryrenesulfonate, polyethylene, polypropylene, polystryrene, and copolymers thereof.

In an aspect, the present disclosure provides methods for making the structures (e.g., multilayer structures). The methods are based on electropolymerization on a conducting substrate. For example, electropolymerization is carried out on a conducting substrate comprising a graphene layer (e.g., a flexible substrate comprising a graphene layer). In an embodiment, the structure (e.g., a multilayer structure) is made by a method disclosed herein.

Figure 3A:
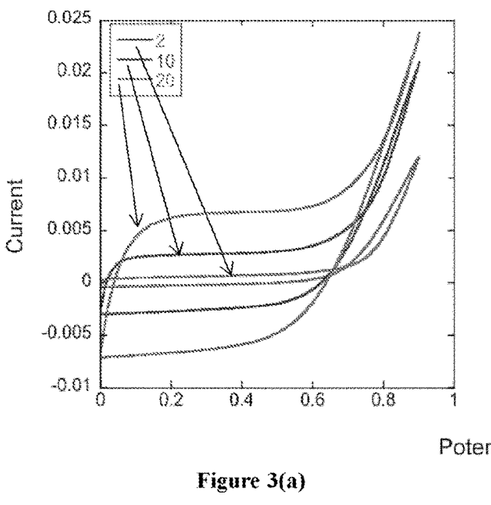
FIG. 3(a). Example of a cyclic voltammogram for electropolymerization of 3,4-ethylenedioxythiophene (EDOT) 10 mM in a 0.1 M tetrabutylammonium perchlorate/acetonitrile solution at a sweep rate of 20 mV/s.
Figure 3B:
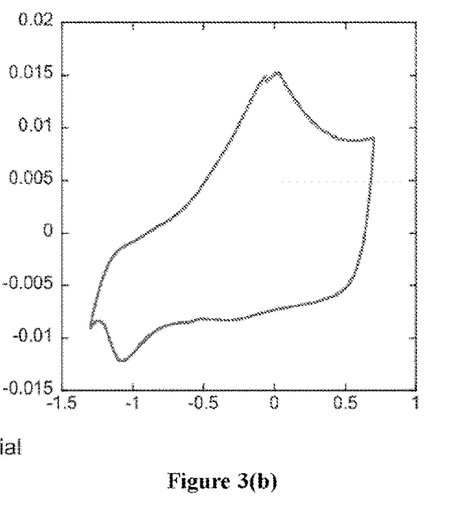
FIG. 3(b). Cyclic voltammogram of the film modified graphene electrode in a 0.1 M tetrabutylammonium perchlorate/acetonitrile solution at a sweep rate of 20 mV/s.
Figure 4A:
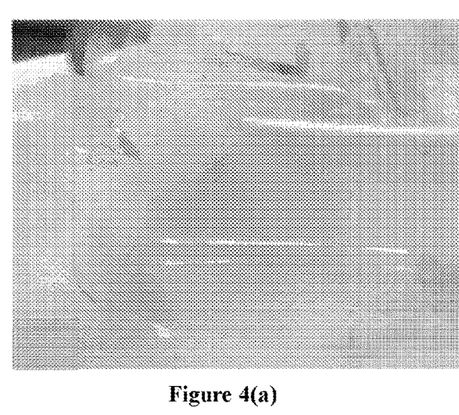
FIGS. 4(a)-4(d). Example of electrochemical cycling of a PEDOT/graphene composite in 0.1 M tetrabutylammonium perchlorate (TBAP)/acetonitrile (AN).
Figure 4B:
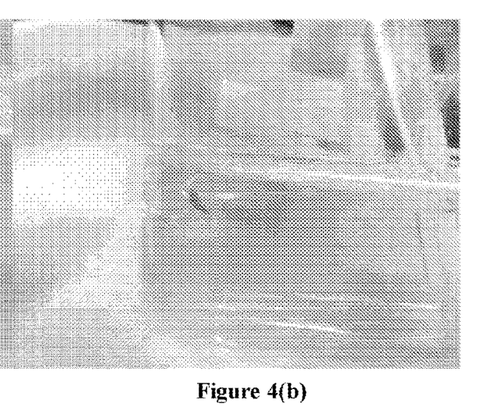
Figure 4C:
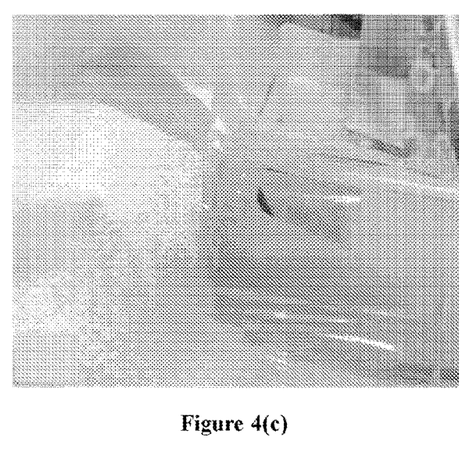
Figure 4D:
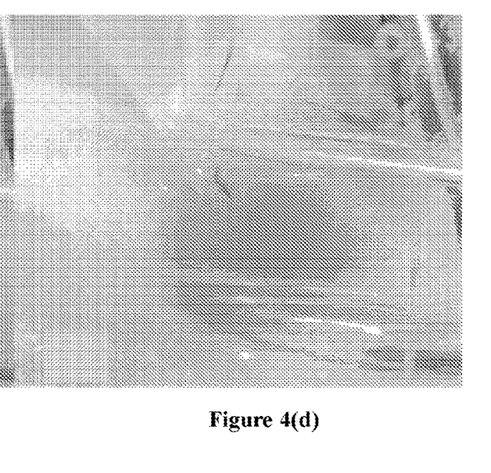

The disclosure involves methodologies by which appropriate monomers can be electropolymerized onto graphene (or any conducting flexible substrate) electrodes taking advantage of the electrosynthesis driven reactions. In FIG. 3A, a cyclic voltammogram illustrating an example of the possible synthetic pathways of electropolymerizing monomers is shown. A 20 mM solution of 3,4-ethylenedioxythiophene (EDOT) is cycled between 0.0V vs Ag/Ag$^+$ and 0.9 V vs Ag/Ag$^+$. The first cycle shows that the monomer onset potential is +0.7 V vs Ag/Ag. Subsequent cycles show a decrease in the onset potential and an increase in the pseudocapacitive current. Both features are characteristic of the electropolymerization of these types of monomers. Moreover, the electropolymerization of these compounds provides advantages in terms of sample preparation, cost and processability, especially when compared to other deposition methods. In addition, by using electropolymerization to modify the graphene (or any conducting flexible substrate) electrodes the conformal coating the electrode material is ensured. It was shown that the monomers used for these experiments can be anodically electropolymerized onto graphene electrodes (FIG. 3B). A cyclic voltammogram of the PEDOT/graphene composite in 0.1 M tetrabutylammonium perchlorate/acetonitrile (TBAP/AN) solution shows the characteristic peaks of a PEDOT film-modified electrode, where the major doping peak can be observed around 0 V vs Ag/Ag$^+$ and the major de-doping peak can be observed at −1.1 V vs Ag/Ag$^+$. The same procedure can be applied to cathodically electropolymerized monomers (e.g., poly-[tris-(4-vinyl-4'-methyl-2,2'-bipyridine)ruthenium]$^{2+}$). Similar anodic and cathodic current responses were observed for other monomer solutions studied (e.g., polythiophene).

Figure 5:
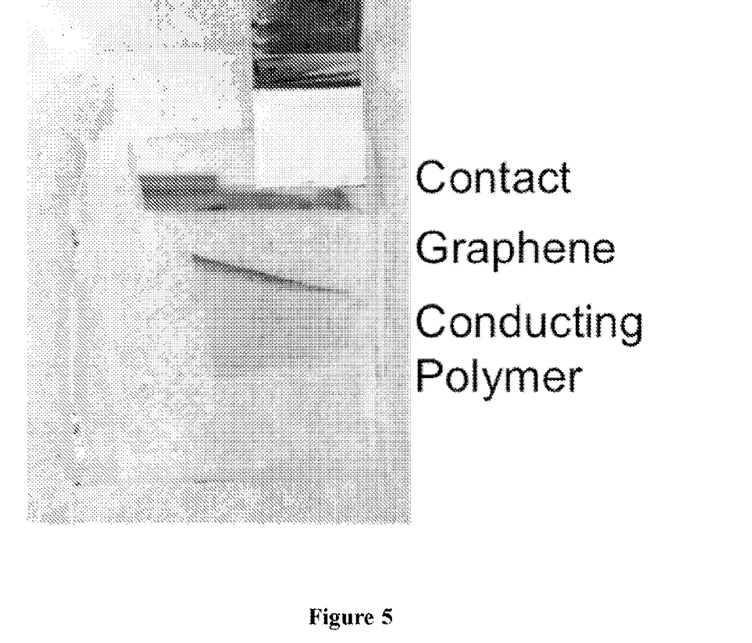
FIG. 5. Image of a film modified graphene electrode.

During the electrochemical cycling, color changes (electrochromism) were observed at the electrode surface (FIG. 4). The color changes for the PEDOT/graphene model system were from blue to clear (going to positive potentials) and from clear to blue in the negative direction. They are represented as different times in the cyclic voltammetry experiment. In FIG. 5, a film-modified graphene electrode is presented. In this figure, the electrode setup used is illustrated and includes the electrical contacts, graphene monolayer and polymer.

In an embodiment, a method of forming a multilayer structure comprising an electropolymerized layer disposed on (i.e., in contact with) at least a portion of, substantially all, or all a conducting substrate (e.g., a graphene layer or portion of a graphene layer) comprises contacting the conducting substrate with a monomer under anodic or cathodic electropolymerization conditions such that an electropolymerized layer is formed on the conducting substrate.

Any monomer that can be electropolymerized can be used. The monomers form polymers upon oxidation or reduction when imposed a potential, or current by the conducting substrate. The monomers can be organic monomers or inorganic monomers (e.g., organometallic compounds and coordination compounds). In an embodiment, the monomer is a thiophene or thiophene derivative, pyrrole or pyrrole derivative, polyfuran or furan derivative, aniline or aniline derivative, phenylenediamine or phenylenediamine derivative, vinyl derivatives (e.g., vinyl-substituted bipyridine metal salts such as poly[tris-(vinyl bipyridine)M], where M is a metal such as, for example, ruthenium, osmium, iron, cobalt, nickel, or rhenium), or a combination thereof.

Examples of suitable monomers include 3,4-(1-thiomethyl)ethylenedioxythiophene; N-methoxyphenylpyrrole (e.g., 1-(4-methoxyphenyl)-pyrrole; N-phenylpyrrole; 3,4-ethylenedioxyselenophene; 3,4-propylenedioxypyrrole; 3,4-ethylenedioxypyrrole; 3,4-dimethoxypyrrole; N-methylpyrrole; pyrrole; 3,4-propylenedioxythiophene; poly(3,4-ethylenedioxythiophene (EDOT); 3,4-dimethoxythiophene; 3-methylthiophene; thiophene; and [tris-(4-vinyl-4'-methyl-2,2'-bipyridine)M]$^{2+}$, where M is a metal such as, for example, ruthenium, osmium, iron, cobalt, nickel, or rhenium. Combinations (i.e., one or more) monomers can be used.

A variety of anodic and cathodic electropolymerization conditions can be used. For example, the electropolymerization is carried out under cyclic voltammetry conditions, potentiodynamic conditions, galvanostatic conditions, and potentiostatic conditions. Employing electropolymerization techniques as a synthetic tool to generate functional polymers enables, for example, the following: control over morphology, film thicknesses, electrical properties, conformal coatings and ensures electronic connectivity between the support and the polymer layer. These properties can be controlled by selection of electropolymerization conditions.

The electropolymerization conditions are such that the monomers are reduced or oxidized and form an electropolymerized polymer layer. In various embodiments, the electropolymerization conditions comprise cycling between a first potential and a second potential two or more times at a constant or varying current, cycling between a first current and second current at a constant potential. The potential and/or current may be pulsed.

In the case of cycling between a first potential and a second potential, the first potential is below the oxidation or reduction potential of at least one monomer (or all of the monomers) and the second potential is above the oxidation or reduction potential of at least one monomer (or all of the monomers). For oxidative polymerizations, the first potential is above the formal potential of at least one monomer and the second potential is below the formal potential of at least one monomer. For the reductive polymerizations, the first potential is below the formal potential of at least one monomer and the second potential is above the formal potential of at least one monomer. In the case of cycling between a first current and second current at a constant potential, the current is sufficient to oxidize or reduce at least one monomer.

The electropolymerization can be carried out for a time sufficient to form an electropolymerized layer. Generally, the rate of polymerization depends on current and potential. Typically, thicker films require longer electropolymerization times.

The substrate (e.g., graphene layer or at least a portion of a graphene layer) is contacted with a monomer under anodic or cathodic electropolymerization conditions in an electrolyte. For example, the electrolyte comprises a solvent and a salt. Examples of suitable salts include lithium perchlorate, sodium chloride, tetrabutylammonium tetraborate, and combinations thereof. Examples of suitable solvents include water, acetonitrile, carbonates, dichloromethane and combinations thereof.

The steps of the methods described in the various embodiments and examples disclosed herein are sufficient to produce the multilayer structures of the present disclosure. Thus, in an embodiment, the method consists essentially of a combination of the steps of the method disclosed herein. In another embodiment, the method consists of such steps.

In an aspect, the present disclosure provides uses of the structures (e.g., multilayer structures). For example, the structures (e.g., multilayer structures) are used in devices.

Figure 6:
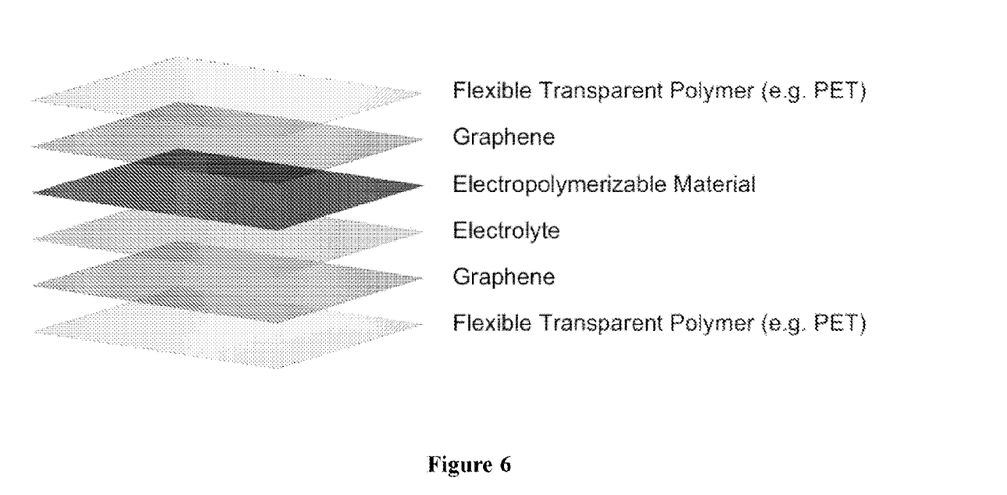
FIG. 6. Example of solid-state flexible device architecture.

For example, for a solid-state device, graphene can be supported by a transparent, flexible, and insulating poly ethylene terephthalate (PET) layer (flexible plastic). A film of the electropolymerizable material can be electro-synthesized onto the graphene electrodes via electropolymerization of its monomer unit. An electrolyte may be added between the two films to form the final device (FIG. 6) whose thickness will be approximately hundreds of micrometers with all of the materials encompassing it being mechanically flexible. These materials and the methodologies employed are important in applications such as, for example, electrochromic devices (FIGS. 4 to 6), electrical energy storage, flexible electronics, flexible displays, light emitting diodes, sensors, and photo-voltaic devices.

In an embodiment, a device comprises a structure (e.g., a multilayer structure) of the present disclosure. The structure (e.g., a multilayer structure) provides a functionality of the device. For example, in an electrochromic device the multilayer structure provides the electrochromic functionality (e.g., the electrochromic material), in energy-storage device the multilayer structures provides the energy storage functionality (e.g., the energy-storage material), and in a photo-voltaic device the multilayer structures provides the photo-voltaic functionality (e.g., the photo-voltaic material). Examples of devices include electrochromic devices, electronic devices, electrical energy-storage devices, energy-generation devices, photo-voltaic devices, and field-effect transistor devices. The devices can be flexible devices. In various embodiments, a device is a display (e.g., a flexible display), light emitting diode (e.g., an organic light emitting diode), sensor, a battery (e.g., a flexible battery), a capacitor (e.g., a flexible capacitor), a supercapacitor (e.g., a flexible supercapacitor).

In an embodiment, a device is a microfluidic device. The microfluidic device can be a sensor or energy generation device.

The following examples are presented to illustrate the present disclosure. They are not intended to limiting in any manner.

Example 1

In this example, examples of the structures (e.g., multilayer structures) of the present disclosure are fabricated and characterized.

Large area, single layer graphene has received much recent interest as an electrode material in electrochemical systems. Examples of large area, single layer graphene platforms for applications such as optical and sensing devices as well as microfluidic systems are shown. Graphene as a protective layer for polymer films during electrogenerated chemiluminescence (ECL) and as a substrate for electrochemical sensing of biomolecules is evaluated. In addition, the fabrication and characterization of a microfluidic device based on single layer graphene electrodes is described. It was found that graphene offers little protection during ECL but offers an alternative electrode material in making optical devices based on polymer films. A working microfluidic device based on a solution-gated field effect transistor was able to detect changes in the pH of aqueous media. A 29 mV shift in the Dirac point per unit pH change was measured with the microfluidic devices, and a ca. 10% FET conductance change was measured when the pH was continuously changed in solution from 6.91 to 7.64 in the microfluidic channel, demonstrating local microfluidic pH sensing in real time.

Large area, single layer graphene electrodes were previously fabricated and electrochemically characterized. These electrodes were used to probe phenomena such as controlling mechanical and chemical defect sites and measuring the 2D surface diffusion coefficient of electroactive adsorbates. To demonstrate the utility of large area, single layer graphene in different electrochemical platforms, optical and sensing devices based on single layer graphene electrodes were demonstrated. Graphene as a protective layer for polymer films during electrogenerated chemiluminescence (ECL), as an electrode material for electrochromic devices based on polymer films, and as a substrate for electrochemical sensing of biomolecules was evaluated. Fabrication and characterization of a working microfluidic device based on electrochemically-gated single layer graphene transistors was demonstrated.

Methodologies for electropolymerizing compounds, viz., 3,4-ethylenedioxythiophene (EDOT), onto large area graphene electrodes through the use of electrochemical techniques such as cyclic voltammetry, chronoamperometry, and galvanostatic methods were developed. Electropolymerization provides advantages in terms of sample preparation, cost, and processing, especially when compared to other chemical and physical deposition methods. The use of electrochemical techniques provides control over materials properties such as thickness, electronic structure, chemical structure, and morphology by simply changing the deposition parameters and conditions. In addition, by using electropolymerization to modify the graphene electrodes, the conformal coating of the electrode material was ensured.

ECL based on organic films is useful in devices such as optical displays and small-molecule sensors. Briefly, ECL is produced when anions and cations of an electroactive, luminescent species that are electrogenerated in close proximity react, provided that sufficient energy is provided to form an excited electronic state, as shown below for annihilation ECL:

$$R^{-\cdot}+R^{+\cdot} \rightarrow R^{*}+R \qquad (1)$$

$$R^{*} \rightarrow R+h\nu \qquad (2)$$

Because these reactions produce visible light, the required energy is typically ca. 2 to 3 eV. Coreactant ECL is induced by a single potential step or a linear potential sweep. A coreactant is used to generate a very reactive species that provides the energy needed to excite the emitting species. Proposed mechanisms are available for a variety of coreactants. One example is the tris(2,2'-bipyridyl)ruthenium(II)/oxalate system, in which a reducing reagent is formed upon sweeping the potential to oxidizing conditions:

$$Ru(bpy)_3^{2+} \rightarrow Ru(bpy)_3^{3+}+e^- \qquad (3)$$

$$Ru(bpy)_3^{3+}+C_2O_4^{2-} \rightarrow Ru(bpy)_3^{2+}+C_2O_4^{-\cdot} \qquad (4)$$

$$C_2O_4^{-\cdot} \rightarrow CO_2^{-\cdot}+CO_2 \qquad (5)$$

$$Ru(bpy)_3^{2+}+CO_2^{-\cdot} \rightarrow Ru(bpy)_3^{+}+CO_2 \qquad (6)$$

$$Ru(bpy)_3^{3+}+Ru(bpy)_3^{+} \rightarrow Ru(bpy)_3^{2+*}+Ru(bpy)_3^{2+} \qquad (7)$$

Coreactant ECL is useful in systems where electrolyte media, such as aqueous solutions, are unstable at potentials necessary to generate the reactive species or if one of the electrogenerated species is unstable.

Polymer films can degrade during ECL due to effects such as dissolution caused by enhanced solubility of the charged film and mechanical breakdown of the film due to incorporation of solvent or counter ions. Particularly, highly reactive radicals which may react with the film are formed during coreactant ECL. In the following studies, graphene as a protective layer at the film/electrolyte interface during ECL of polymer films was considered. Large area graphene has already been studied as a protective layer for metals and semiconductors under thermally and electrochemically oxidizing conditions although passivation of metals such as copper was limited to several hours. ECL at ITO electrodes modified using poly Ru(v-bpy)$_3^{2+}$ was investigated, where v-bpy is 4-vinyl, 4'-methyl bipyridine, as a model system since the ECL of surface-immobilized Ru(bpy)$_3^{2+}$ is well-documented and films of electropolymerized Ru(v-bpy)$_3^{2+}$ can be grown readily. Coreactant ECL was considered in order to probe electron transfer processes across graphene, requiring interaction of a solution species, viz., the coreactant, through the graphene layer with immobilized Ru(v-bpy)$_3^{2+}$ films.

Another useful area of polymer-modified electrodes is in biosensing. Polymer films have been used as antifouling agents as well as providing a soft platform for antibody detection. In these studies, sensors based on nicotinamide adenine dinucleotide (NADH) were considered because NADH is involved in over 200 known enzymatic reactions, making it a popular analyte, and glassy carbon modified with polymerized 3,4-dihydroxybenzaldehyde (DHB) catalyzes its oxidation. NADH oxidation has already been documented at graphene-composite electrodes.

In addition to polymer-modified graphene platforms, construction of a graphene sensing platform was demonstrated on which the solution-gated field effect transistor was integrated into a microfluidic system to achieve local pH sensing. Graphene is a two dimensional material that is fully comprised of surfaces. The electrical conductance of graphene is thus sensitive to the changes of charge environment induced by analyte reaction or absorption on the graphene surface, and is often used as a readout for various graphene-based sensing devices. The high charge carrier mobility of graphene imparts lower noises and thus better sensing performance in graphene-based sensing device. In solution-gated graphene field effect transistors, the graphene surface is directly exposed to the solution and the gate voltage is applied electrochemically to graphene through the Debye layer at the graphene/electrolyte interface. Due to the relatively large capacitance of the Debye layer, changes of the gate voltage induced by a chemical change in solution is expected to lead to significant changes of the graphene charge carrier density, and consequently the graphene conductance. Solution-gated field effect transistors have been extensively studied for pH sensing. A moderate response of 6-20 mV shift in the Dirac point per unit pH change was typically observed. The corresponding change of graphene conductance was found to be 3-13% per unit pH change, when compared to the conductance at pH 7 at gate voltages close to the Dirac point.

Experimental Methods. Materials. All chemicals were used as received unless otherwise noted. Tripropylamine (TPrA) (≥98%), 3,4-ethylenedioxythiophene (EDOT), tetrabutylammonium hexafluorophosphate (TBAPF$_6$) (for electrochemical analysis, ≥99.0%), tetrabutylammonium perchlorate (TBAP) (for electrochemical analysis, ≥99.0%), anisole (anhydrous, 99.7%), Tris base (tris(hyrdoxymethyl) aminomethane), and acetonitrile (MeCN) (anhydrous, 99.8%), were from Sigma-Aldrich (St. Louis, Mo.). Strem Chemicals (Newbury Point, Mass.) was the supplier of tris(2,2'-bipyridyl)ruthenium(II) chloride hexahydrate, [Ru(bpy)$_3$]$^{2+}$ (min. 98%). Purified [Ru(v-bpy)$_3$](PF$_6$)$_2$ was from an available batch. Reduced nicotinamide adenine dinucleotide (NADH) (grade II, 98%) disodium salt was from Roche Diagnostics (Indianapolis, Ind.). Sodium oxalate (Na$_2$C$_2$O$_4$), sodium acetate, sodium phosphate monobasic, sodium phosphate dibasic, sodium nitrate, acetone, isopropanol, and dichloromethane were all analytical reagent grade and from Mallinkrodt-Baker (Phillipsburg, N.J.). 3,4-DHB (97%) was from Pfaltz and Bauer (Waterbury, Conn.). Silicon wafers with a 300 nm layer of thermally grown oxide (Si/SiO$_2$) were from Silicon Quest International (San Jose, Calif.), and 1.1 mm glass slides coated with tin-doped indium oxide (ITO) (10 Ω/cm$^2$) were from Nanocs Inc. (New York, N.Y.). Water (18 MΩ·cm) purified using a Millipore (Billerica, Mass.) Milli-Q system was used to clean all glassware and to prepare all aqueous solutions.

Graphene was grown on 0.025 mm thick copper foil (99.8%, Alfa-Aesar, Ward Hill, Mass.) using known chemical vapor deposition (CVD) methods. A layer of poly(methyl methacrylate) (PMMA) was added to the graphene before etching the copper in order to provide support during transfer. After etching the copper and transferring to water at least six times, graphene/PMMA was transferred to Si/SiO$_2$, ITO, modified ITO (vide infra), or a glass microscope slide and dried with nitrogen. To remove the PMMA, the chips were immersed first in anisole for two to three hours, then in 50/50 (v/v) dichloromethane/acetone for at least 12 hours, and finally in isopropanol for at least two hours. The quality of the single layer graphene was verified by the 2D and G peaks at 2700 and 1600 cm$^{-1}$, respectively, in the Raman spectra, obtained using a Renishaw (Gloucestershire, UK) InVia Confocal Raman microscope with excitation wavelength of 488 nm.

Figure 7:
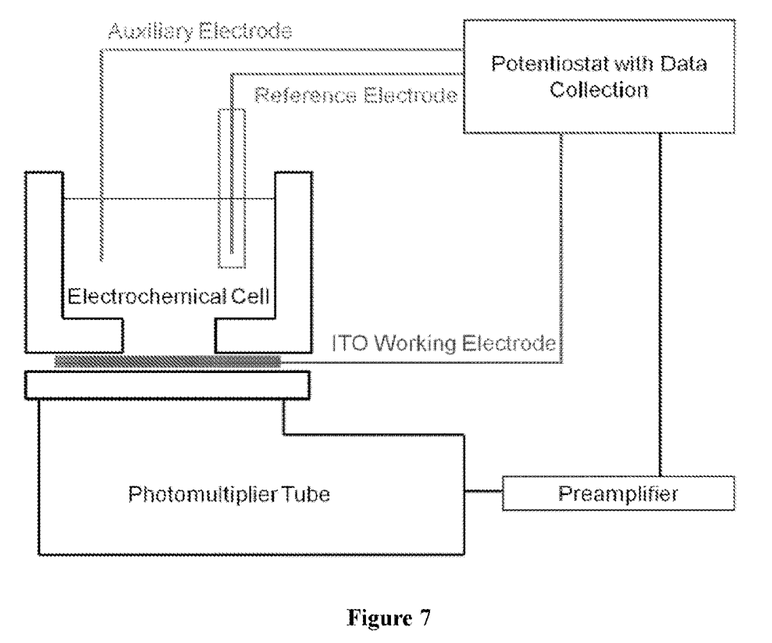
FIG. 7. Example of a diagram of equipment for detecting ECL emission. ECL generated in the electrochemical cell is detected by the photomultiplier tube placed directly below the cell, opposite to the electrolyte solution.

Electrochemical and ECL Measurements. All electrochemical measurements were performed in a three-electrode cell configuration with graphene as the working electrode. Electrical contact to graphene was made using gold evaporated on the graphene or by using copper tape and indium wire directly on the graphene. Auxiliary and reference electrodes were a gold or platinum wire and an Ag/AgCl/1 M KCl electrode inside a salt bridge (3% agar with 0.2 M potassium nitrate), respectively. All potentials are reported vs. Ag/AgCl unless noted otherwise. A silver wire quasireference electrode (Ag QRE) was used in nonaqueous solutions. No calibration of the QRE was made because the potential was usually stable over the time required for each measurement. Electrodes were placed in a homemade Teflon cell with a Plexiglas base, and an o-ring was used to expose an area of 0.5 cm$^2$ graphene to solution. For ECL measurements, the base was an aluminum piece with a hole to allow any emitted light to pass through the bottom of the cell. In this configuration, any ECL emission was detected through the ITO electrode on the bottom of the cell opposite to the solution (FIG. 7).

ECL measurements were performed using an EG&G Princeton Applied Research (Princeton, N.J.) Model 173 Potentiostat-Galvanostat with a Model 175 Universal Programmer and Model 176 Current Follower. Data were recorded using a custom LabVIEW (National Instruments, Austin, Tex.) program and a National Instruments USB-6210 DAQ device. Emission was detected using a Hamamatsu Model R928 photomultiplier tube (PMT) operated at 750 V using a Model 556 high-voltage power supply from EG&G Ortec (Oak Ridge, Tenn.). The PMT was connected to the DAQ device using an Ithaco (Ithaca, N.Y.) Model 1211 current preamplifier.

Electrochromic measurements were performed at room temperature using a Model HSV-100 and HABF1510m potentiostat (Hokuto Denko). All other electrochemical measurement were performed using a Model 900 potentiostat (CH Instruments, Austin, Tex.).

Polymer Film Growth for Electrochemical Measurements. Films of poly-Ru(v-bpy)$_3^{2+}$ were made through electroreductive polymerization by immersing ITO in a solution of 0.5 mM solution of [Ru(v-bpy)$_3$](PF$_6$)$_2$, in 0.1 M TBAPF$_6$ in acetonitrile and cycling the potential between 0.2 V and 1.8 V vs. the Ag QRE, just past the second reduction wave of Ru(v-bpy)$_3^{2+}$, which is the first ligand reduction. The potential was typically cycled at a scan rate of 100 mV/s. After electropolymerization, the electrode was removed from the Ru(v-bpy)$_3^{2+}$ solution and rinsed with acetone. ITO/poly-Ru(v-bpy)$_3^{2+}$, i.e., the ITO modified with poly-Ru(v-bpy)$_3^{2+}$, was then immersed in fresh electrolyte solution or graphene was transferred over the polymer layer as described previously.

3,4-DHB films were grown through electrooxidative polymerization by cycling the potential of graphene on Si/SiO$_2$ between 0.2 and +0.8 V vs. Ag/AgCl for 5 cycles in a solution of 1 mM 3,4-DHB in 0.1 M Tris buffer, pH 8.21, with 0.1 M NaNO$_3$. After rinsing with water, the electrode was immersed in fresh buffer or buffer containing NADH.

Figure 8A:
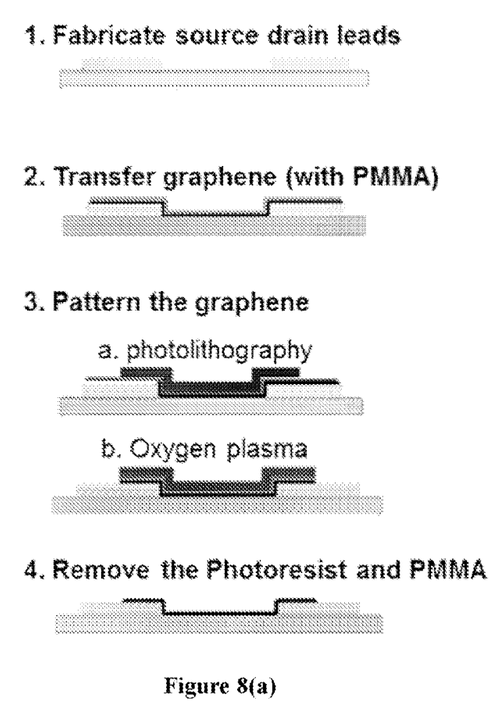
FIG. 8(a) Fabrication steps for graphene FET.
Figure 8B:
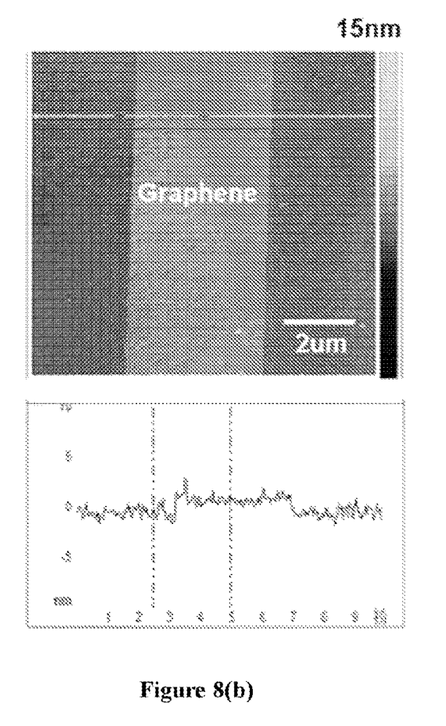
FIG. 8(b) AFM characterization of graphene surface after patterning.

Microfluidic Device Fabrication and Characterization. Fabrication of Graphene Field Effect Transistor. For the fabrication of graphene field effect transistors, metal electrodes made of 5 nm of Ti and 200 nm of Au were first patterned on a fused silica substrate using photolithography and electron beam evaporation (FIG. 8a; step 1). CVD graphene was then transferred onto the fused silica substrate to make electrical contact with the metal electrodes using the same processes as those for ECL sample preparation, except that the PMMA supporting layer was kept on top of the graphene (FIG. 8a; step 2). In the next step, (FIG. 8a; step 3) the graphene was patterned into a rectangular stripe using photolithography and oxygen plasma. Since the PMMA was not removed in the earlier step, the oxygen plasma patterned graphene by first removing the PMMA and then the underneath graphene. This fabrication scheme avoided the direct contact of photoresist with graphene and was capable of obtaining cleaner graphene surfaces. In the last step, the photoresist and PMMA on graphene strips were removed by heated 1165 solution (70-80 degrees) for 1 hour. The devices were then rinsed with isopropanol and blown dry with N$_2$ (FIG. 8a; step 4). FIG. 2b shows the AFM image of graphene sample patterned with the above method. The CVD graphene surface remained smooth and clean after the patterning step.

Figure 9A:
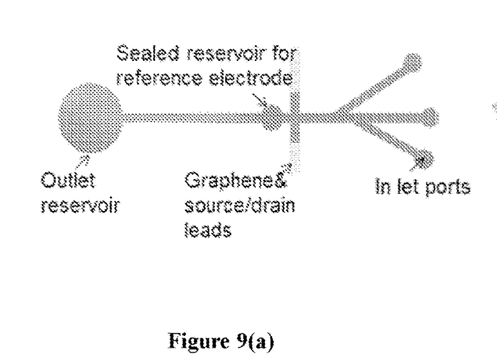
FIG. 9(a) Path of the microfluidic channel.

Microfluidic Solution-Gated Graphene FET Construction and Measurement Schemes. For the microfluidic solution-gated graphene FET devices, PDMS microfluidic channels that are 200 μm in width and 40 μm in height with multiple inlet ports and one outlet reservoir were fabricated using standard methods. A close sealed reservoir was placed along the channel for reference electrode insertion (FIG. 9a). To construct the microfluidic device, the polydimethylsiloxane (PDMS) block was treated with oxygen plasma and then bonded to a freshly fabricated graphene FET. The two compartments are carefully aligned to ensure the microfluidic channel right above the graphene stripe (FIG. 9c, inset). A platinum wire used as reference electrode was punched into the sealed reservoir and further sailed with epoxy (FIGS. 9b and 9c).

During measurement, buffer solutions with known pH were injected into the microfluidic channel via the inlet port at a controlled flow rate of <~15 μL/minute. A gate voltage (0-0.5V) was applied to the graphene FET through the Pt reference electrode, while the conductance of graphene was monitored through the metal electrodes with constant source-drain voltage of 5 or 10 mV.

Figure 9B:
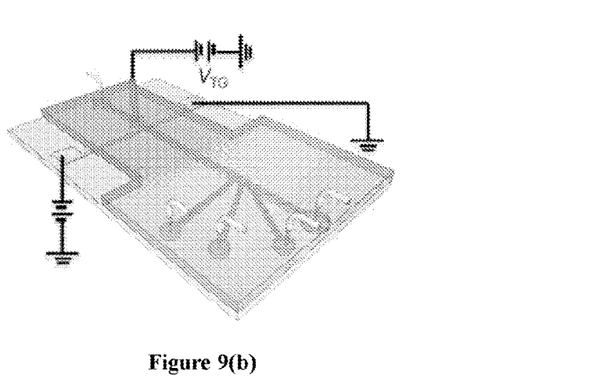
FIG. 9(b) Structure of the microfluidic graphene FET and measurement scheme.
Figure 9C:
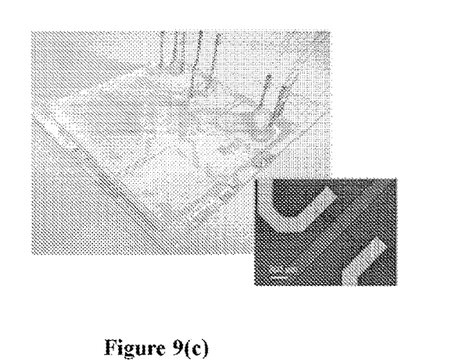
FIG. 9(c) Optical image of a assembled microfluidic graphene FET.

FIG. 9b illustrates the structure of the microfluidic device together with our electrical measurement scheme. FIG. 9c shows the optical image of the microfluidic device after construction. To make good use of a single piece of CVD graphene and the fabrication resources, 8 devices were fabricated in parallel processes on a quarter of a 4 inch fused silica substrate.

Figure 9D:
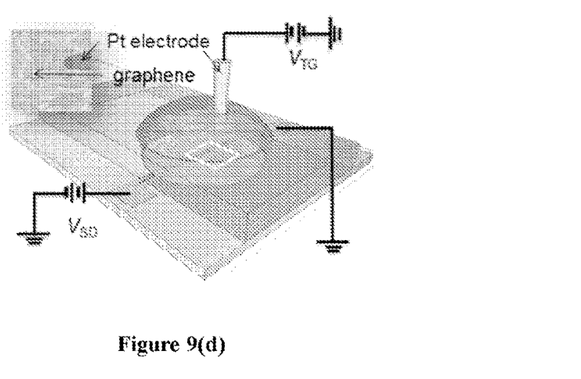
FIG. 9(d) Structure and measurement scheme of the solution-gated FET in an inverted cell structure.

Solution-gated Graphene FET in Inverted Cell Structure for System Characterization. A solution-gated graphene FETs in an inverted cell structure was constructed to more easily characterize the pH sensitivity of the solution-gated graphene FETs. This kind of device was constructed by placing a PDMS open reservoir (6 mm in diameter) directly on top of the graphene FET. During measurement, the reservoir was filled with solutions with known pH, and the Pt wire was directly inserted to the reservoir. FIG. 9d illustrates the structure of the microfluidic device together with the electrical measurement scheme.

Graphene as a Protective Blanket for ECL Platforms. For ECL, ITO was used as the supporting substrate in place of Si/SiO$_2$ because ITO is conductive, allowing facile polymer growth, and transparent, allowing for light transmission. Measurements were performed on ITO modified with poly-Ru(v-bpy)$_3^{2+}$ and/or graphene in solutions of two different coreactants, tripropylamine (TPrA) and C$_2$O$_4^{2-}$. The surface coverage, Γ, of poly-Ru(y-bpy)$_3^{2+}$ was determined using the charge passed by the Ru$^{2+/3+}$ couple in a cyclic voltammogram of the film immersed in fresh electrolyte. The area is related to the charge, Q, of an electroactive species immobilized on an electrode. From Q, the surface coverage is calculated from the following equation:

$$Q = nFA\Gamma \quad (1)$$

where n is the number of electrons passed per redox active group (n=1 for poly-Ru(v-bpy)$_3^{2+}$), A is the area of the electrode (0.5 cm$^2$) and F is Faraday's Constant (96485 C/mole e$^-$). Values of Γ were typically between 1.5×10$^{-10}$ and 1.5×10$^{-9}$ mol/cm$^2$, as controlled by the number of potential cycles, corresponding to 2 to 18 monolayers with a thickness between 2.8 and 25.6 nm, assuming that each monolayer is 8.3×10$^{-11}$ mol/cm$^2$ and is 1.42 nm thick.

Figure 10A:
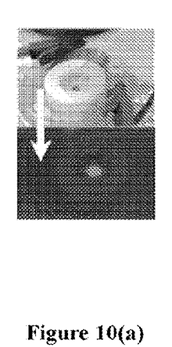
FIG. 10(a) Image of ECL of graphene on Si/SiO$_2$ in electrochemical cell with 0.2 mM Ru(bpy)$_3^{2+}$ and 0.1 M TPrA. Applied potential, +1.4 V vs. Ag/AgCl.
Figure 10B:
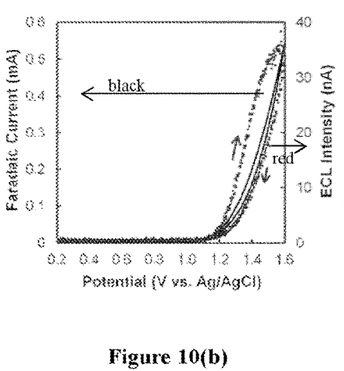
FIG. 10(b) Faradaic current (black) and ECL emission (red) of bare ITO exposed to a solution of 0.2 mM Ru(bpy)$_3^{2+}$ and 0.1 M TPrA as a function of applied potential.
Figure 10C:
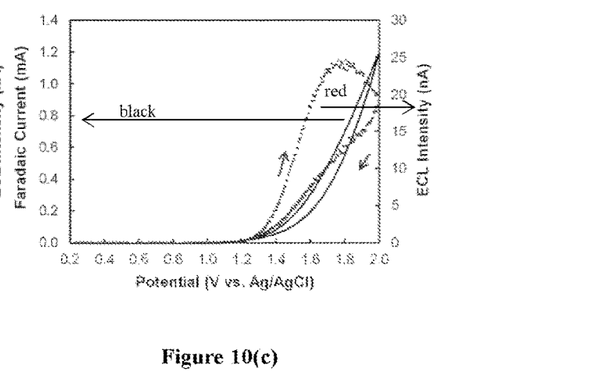
FIG. 10(c) Faradaic current (black) and ECL emission (red) of ITO covered with single layer graphene exposed to a solution of 0.2 mM Ru(bpy)$_3^{2+}$ and 0.1 M TPrA as a function of applied potential. Scan rate, 50 mV/s; supporting electrolyte, 0.2 M phosphate buffer, pH 7.0; electrode area, 0.5 cm$^2$.

ECL with TPrA. Studies of coreactant ECL were started at graphene using TPrA in 0.2 M phosphate buffer, pH 7.0. Visible, orange light was observed at single layer graphene on Si/SiO$_2$ immersed in a solution of Ru(bpy)$_3^{2+}$ and TPrA (FIG. 10a) with an applied potential of +1.4 V vs. Ag/AgCl for at least 10 minutes, indicating that graphene is stable under these conditions. The ECL intensity was similar at bare ITO and ITO/graphene (FIGS. 10b and 10c), indicating that graphene does not significantly quench ECL.

Figure 11A:
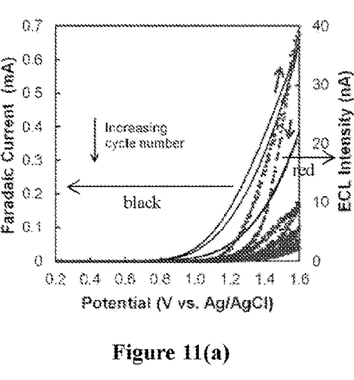
FIG. 11(a) Faradaic current (black line, first and seventh cycles shown) and ECL emission (red) as a function of potential of an ITO modified with poly-Ru (v-bpy)$_3^{2+}$ exposed to a solution of 0.13 M TPrA.
Figure 11B:
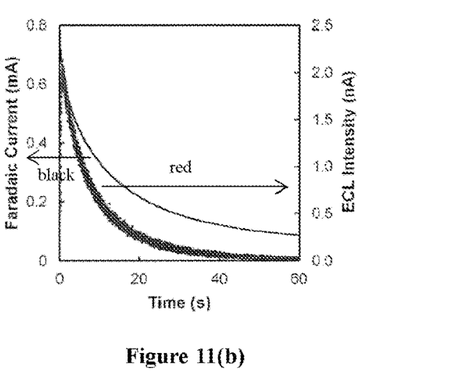
FIG. 11(b) Faradaic current (black) and ECL emission (red) as a function of time for the ITO/poly-Ru(v-bpy)$_3^{2+}$ exposed to a solution of 0.13 M TPrA. Applied potential, +1.2 V vs. Ag/AgCl.

FIG. 11a shows ECL as a function of potential for ITO/poly-Ru(v-bpy)$_3^{2+}$ exposed to TPrA. Upon potential cycling, the ECL intensity decreased, with a 75% loss in signal observed in the second cycle. Chronoamperometry indicates that emission was no longer detected after 60 sec (FIG. 11b), indicating that the film is unstable under our experimental conditions. Indeed, ca. 80% of the charge for the Ru$^{2+}$/Ru$^{3+}$ couple in the immobilized film was lost after the first cycle, which could be due to film dissolution or that the film simply became inactive, as has been reported in the presence of Ru$^{1+}$ species. These results are in contrast to annihilation ECL in acetonitrile, in which emission was observed for at least 20 minutes of a poly-Ru(v-bpy)$_3^{2+}$.

Figure 11C:
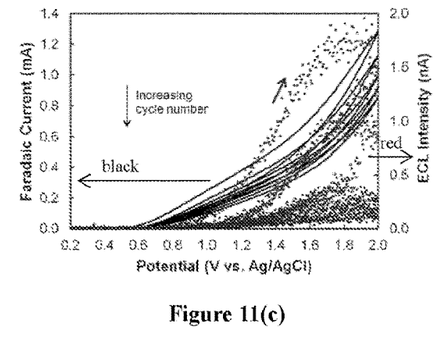
FIG. 11(c) Faradaic current (black) and ECL emission (red) as a function of potential of the ITO/poly-Ru(v-bpy)$_3^{2+}$/graphene in 0.13 M TPrA. Scan rate, 50 mV/s; supporting electrolyte, 0.2 M phosphate buffer, pH 7.0; electrode area, 0.5 cm$^2$.

With a single layer of graphene placed between the poly-Ru(v-bpy)$_3^{2+}$ and electrolyte solution, i.e., ITO/poly-Ru(v-bpy)$_3^{2+}$/graphene, ECL emission decreased upon potential cycling, similar to the results for the bare ITO/poly-Ru(v-bpy)$_3^{2+}$, with a 50% decrease in signal upon the second cycle (FIG. 11c). Therefore, single layer graphene offers little protection in the presence of TPrA. Raman spectra show the characteristic G and 2D peaks near 1600 and 2700 cm$^{-1}$, indicating that graphene was present before and after ECL. These results suggest that loss in ECL intensity is due to the film itself and that graphene did not decompose during ECL although it is expected that graphene, as with other carbon materials, is probably oxidized at the potential applied.

ECL with $C_2O_4^{2-}$. Because poly-Ru(v-bpy)$_3^{2+}$ became inactive during ECL with TPrA, $C_2O_4^{2-}$ was pursued as the coreactant. These measurements were performed in 0.1 M acetate buffer, pH 4.6, which is at a lower pH than the TPrA measurements at pH 7.0. These conditions should be less oxidizing, and therefore less aggressive, at the same applied potentials. In addition, Ru(bpy)$_3^{2+}$ immobilized in Nafion films, in which ECL was observed for over 1500 cycles using $C_2O_4^{2-}$ in aqueous solution.

Cyclic voltammetry and chronoamperometry (FIGS. 12a and 12b) of ITO/poly-Ru(v-bpy)$_3^{2+}$ exposed $C_2O_4^{2-}$ show that a 25% loss in ECL intensity occurred upon the second cycle and that ECL emission was detected without a diminishing signal for over two minutes under applied potential at +1.4 V vs. Ag/AgCl. In addition, 80% of the original charge in the Ru$^{2+}$/Ru$^{3+}$ couple remained after ECL. These results demonstrate that the films are more stable with $C_2O_4^{2-}$ as the coreactant. However, as with TPrA, a decrease in ECL intensity was observed even when single layer graphene was transferred on top of the film (FIGS. 12b and 12d).

Figure 12A:
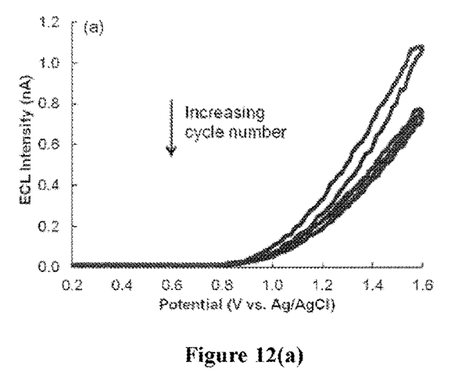
FIG. 12(a) Example of ECL emission as a function of potential of an ITO modified with poly-Ru (v-bpy)$_3^{2+}$ exposed to a solution of 50 mM C$_2$O$_4^{2-}$.
Figure 12B:
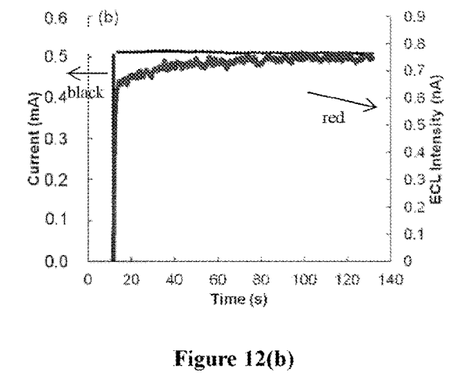
FIG. 12(b) Faradaic current (black) and ECL emission (red) as a function of time for the ITO/poly-Ru(v-bpy)$_3^{2+}$ exposed to a solution of 50 mM C$_2$O$_4^{2-}$. Applied potential, +1.4 V vs. Ag/AgCl.
Figure 12C:
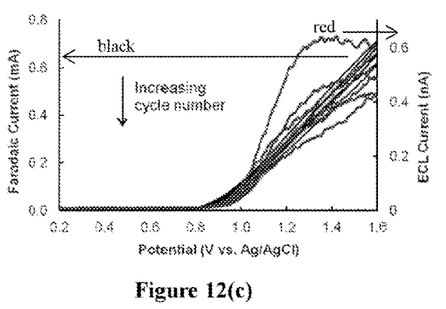
FIG. 12(c) Faradaic current (black) and ECL emission (red) as a function of potential of the ITO/poly-Ru(v-bpy)$_3^{2+}$/graphene in 50 mM C$_2$O$_4^{2-}$.
Figure 12D:
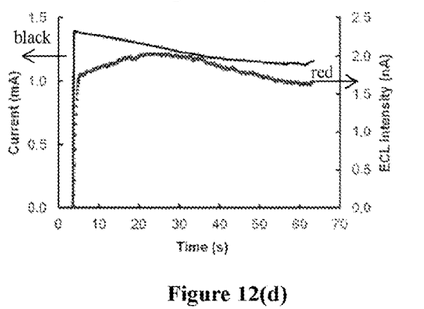
FIG. 12(d) Faradaic current (black) and ECL emission (red) as a function of time for the ITO/poly-Ru(v-bpy)$_3^{2+}$/graphene exposed to a solution of 50 mM C$_2$O$_4^{2-}$. Applied potential, +1.4 V vs. Ag/AgCl. Scan rate, 25 mV/s; supporting electrolyte, 0.1 M acetate buffer, pH 4.6; electrode area, 0.5 cm$^2$.

It is interesting to note that the cyclic voltammetric profile is different for the bare polymer film and for that covered with graphene over the same potential range (FIGS. 12a and 12c). The peak shape in the cyclic voltammogram of the graphene-covered film is reminiscent of a mass transport-limited reaction such as a solution species diffusing to an array of ultramicroelectrodes. It is possible that the coreactant diffuses to the underlying polymer film exposed to solution through physical holes in the graphene. However, the fact that the ECL intensities of the bare and covered films are of the same order of magnitude suggests that ECL probably originates from more than just sites with holes. Perhaps the coreactant diffuses through the holes and becomes sandwiched between the graphene and polymer film.

Although graphene seemed to offer little improvement as a protective layer in ECL, it may be interesting to consider graphene as a contact material in luminescence devices. It has been demonstrated that processes such as metal deposition affect the behavior of electroluminescent devices, possibly due to film degradation during the deposition process. Large area graphene may offer a more gentle way of introducing the top contact electrode in these systems.

Electropolymerization of EDOT on Graphene for Electrochromic Applications. Electropolymerization of materials onto graphene electrodes has similarities to electropolymerization onto conducting substrates in general (FIG. 3A). A 20 mM solution of EDOT was cycled between 0.0V vs. Ag/Ag$^+$ and +0.9 V vs. Ag/Ag$^+$. The first cycle shows that the monomer onset potential is +0.7 V vs. Ag/Ag$^+$. Subsequent cycles show a decrease in the onset potential and an increase in the pseudocapacitive current. Both features are characteristic of the electropolymerization of these types of monomers. Our results indicate that the monomers used for these experiments can be anodically electropolymerized onto graphene electrodes (FIG. 3B). A cyclic voltammogram of the PEDOT/graphene composite in 0.1 M TBAP/MeCN solution shows the characteristic peaks of a PEDOT film-modified electrode, where the major doping peak can be observed around 0 V vs. Ag/Ag$^+$ and the major de-doping peak can be observed at −1.1 V vs. Ag/Ag$^+$. Similar anodic and cathodic current responses were observed for other monomer solutions studied, e.g., polythiophene.

During the electrochemical cycling, color changes, i.e., electrochromism, were observed at the electrode surface (FIG. 4). Upon application of positive potentials, the PEDOT/graphene model system faded from blue to a colorless film, and this color change could be reversed by scanning in the negative direction. In FIG. 5, a film-modified graphene electrode is presented. In this figure, the electrode setup used is illustrated and includes the electrical contacts, graphene monolayer and polymer.

Figure 13A:
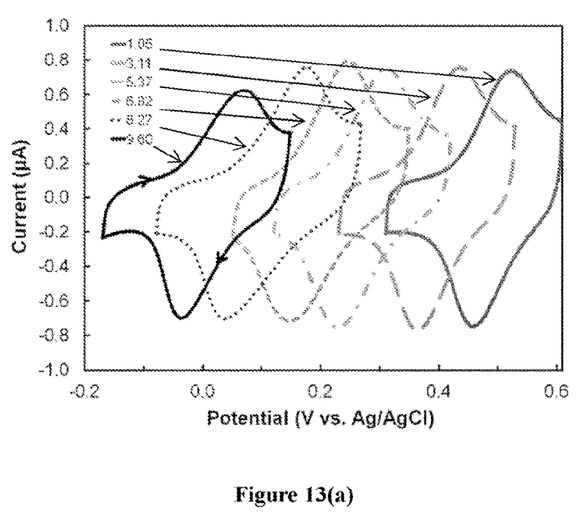
FIG. 13(a) Cyclic voltammograms of a 3,4-DHB-modified graphene electrode on Si/SiO$_2$ in buffer at various pH values. Sweep rate, 100 mV/s; supporting electrolyte, 0.1 M acetate or Tris buffer with 0.1 M NaNO$_3$; electrode area, 0.5 cm2.
Figure 13B:
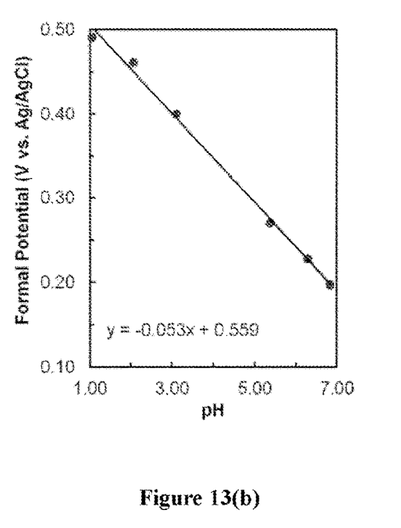
FIG. 13(b) Corresponding plot of formal potential vs. pH value.

NADH Oxidation at 3,4-DHB-Modified Graphene. To test large area graphene as an electrochemical sensor, oxidation of NADH was measured at bare single layer graphene and graphene modified with 3,4-DHB. 3,4-DHB-modified graphene exhibited well-behaved surface anodic and cathodic waves, corresponding to the two electron oxidation and reduction, respectively, of the quinone functionalities, in 0.1 M acetate or Tris buffer with 0.1 M NaNO$_3$ at different pH values ranging from 1.05 to 10.53 (FIG. 13). A plot of the peak current vs. the sweep rate was linear, indicating that the 3,4-DHB films were immobilized to graphene. Typical surfaces coverages were ca. $5 \times 10^{-12}$ mol/cm$^2$, calculated using Equation 1 with n=2. The formal potential, $E^{0'}$, was estimated as the average of the cathodic and anodic peak potentials. Similar to results reported by Pariente et al., the slope of $E^{0'}$ vs. pH changed above pH 6.82, which was attributed to the first deprotonation of the quinones. For pH values below 7, $E^{0'}$ shifts negative by 53 mV per pH unit (FIG. 13b), corresponding to a 59 mV/pH unit expected for two electrons transferred per two protons, in agreement with the literature. $\Delta E_{peak}$ increased with increasing pH, suggesting that the electron transfer kinetics become slower as the concentration of protons decreases. It should be noted that the DHB films desorb upon potential cycling, indicated by a decrease of ca. 15% in the surface coverage after 30 minutes in phosphate buffer. This desorption was attributed to the increased solubility of the deprotonated, charged polymer.

Figure 14:
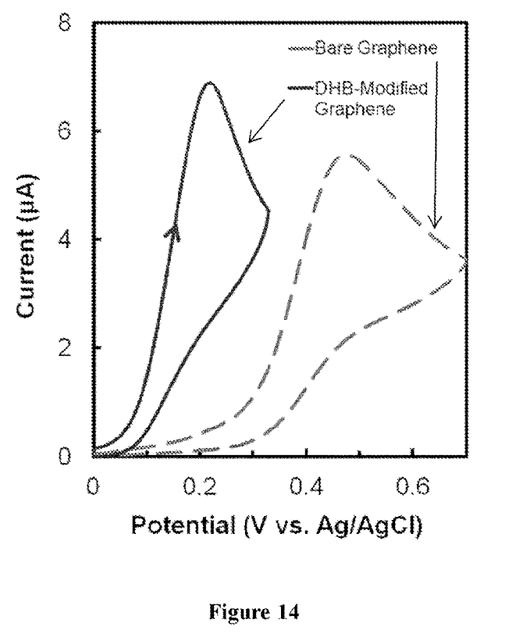
FIG. 14. Typical cyclic voltammograms of 0.5 mM NADH at bare graphene and a 3,4-DHB-modified graphene. Sweep rate, 5 mV/s; supporting electrolyte, pH 7.5 phosphate buffer; electrode area, 0.5 cm$^2$.
Figure 15A:
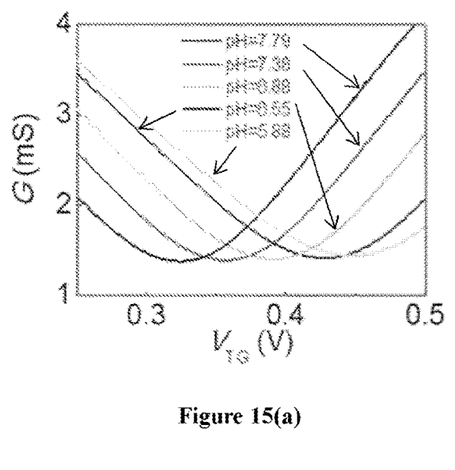
FIG. 15(a) Gate-dependent FET conductance measured with an inverted-cell device in phosphate buffers at different pH.
Figure 15B:
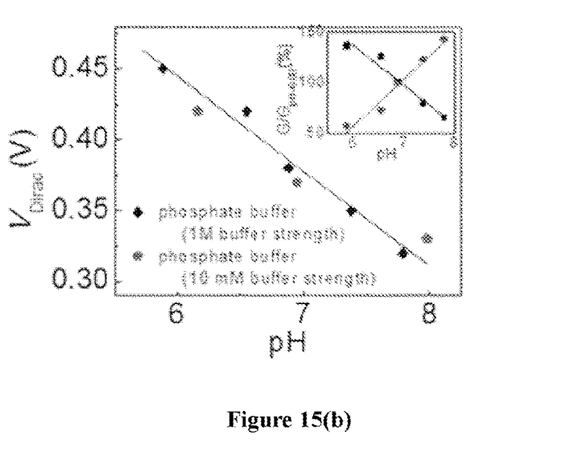
FIG. 15(b) Dirac point gate voltage as a function of pH for two different groups of buffer solutions. Inset: The conductance of the device shown in FIG. 15(a) as a function of pH value at gate voltage of 0.30V and 0.50V.

One anodic wave at +0.47 V vs. Ag/AgCl was observed at bare graphene immersed in 0.5 mM NADH in pH 7.5 phosphate buffer (FIG. 14), corresponding to the oxidation of NADH to NAD$^+$, similar in potential to that previously observed. At 3,4-DHB-modified graphene, this wave shifted negative by 250 mV and the peak current increased about 20%, indicating that NADH oxidation at graphene is catalyzed in the presence of 3,4-DHB. A similar enhancement was observed in NADH oxidation activity was observed for chemically-reduced graphene modified with methylene green.

pH Sensing with Graphene Microfluidic Devices. pH Sensitivity of Solution-Gated FETs in the Inverted Cell Structure. A solution-gated graphene FETs in an inverted cell structure was constructed to study the intrinsic pH sensitivity of our microfluidic devices. FIG. 15a shows the conductance of an inverted-cell device as a function of the gate voltage in bulk volumes of phosphate buffer solutions of different pH values. For each fixed pH condition, a "V" shaped, p- to n-type transition was observed as the Pt top-gate voltage $V_{TG}$ was scanned, and the conductance curves shift to more negative potentials at higher pH values. A good linearity is observed when the measured Dirac point gate voltage, as defined by the conductance minimum, is plotted as a function of the pH value, for data obtained across different buffer solutions over a large pH range of 5.9 to 8 (FIG. 15b). Notably, a high pH sensitivity of ~60 mV shift of Dirac point voltage per unit pH change was observed for our solution gated graphene FET device. This value is 2-3 times larger than the typical value obtained in previously studies.

FIG. 12b includes experimental data measured in two groups of buffer solutions with different buffer types and buffer capacity. All data points fall on the same line, indicating good reliability of the solution-gated graphene FETs as a pH sensor. The measured conductance of graphene was plotted as a function of pH for gate voltage at 0.3V and 0.5V. The graphene conductance changed by −40% per unit pH and 45% per unit pH, respectively, for the two fixed gate voltages, compared to the measured conductance at pH 6.88. This value is again approximately 3-4 times larger the previously reported values.

Figure 15C:
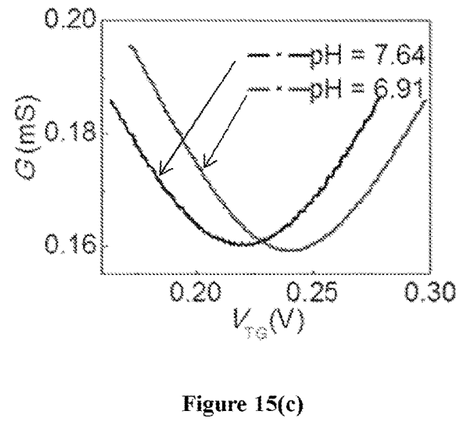
FIG. 15(c) Gate-dependent FET conductance measured with a microfluidic device at two different pH values.
Figure 15D:
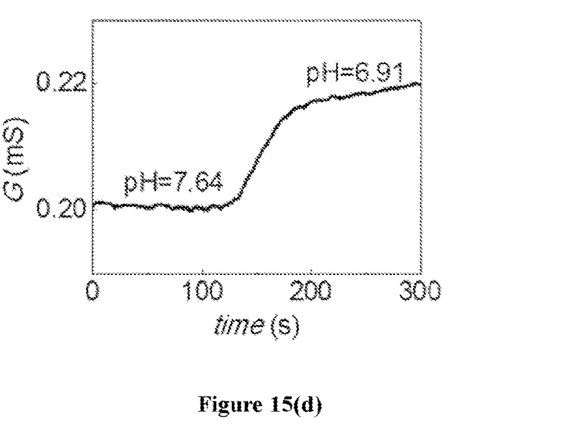
FIG. 15(d) Continuous monitoring of the conductance of a microfluidic device when solution pH changes from 7.64 to 6.91.

Since all previous studies used Ag/AgCl reference electrodes for gate application, it was suspected that usage of Pt wire instead of Ag/AgCl electrodes contributes to the enhanced sensitivity of the device. The half-cell voltage at Pt/solution interface, in this case, senses the pH of solution in addition to the half-cell voltage at graphene/solution interface.

pH Sensitivity of Solution-Gated FETs in Microfluidic Devices. Integrating the solution-gated FETs to in a microfluidic system enables us to detect the local pH value in the system. FIG. 15c shows the gate-dependence data obtained with our microfluidic device at two different pH values. The Dirac point voltage changed by 21 mV when the solution pH value changes from 7.64 to 6.91, corresponding to ca. 29 mV per unit pH change. This value is smaller than what was obtained with solution-gated FETs in the inverted cell structure, but is still larger than the typical values from previous studies. FIG. 15d shows continuous measurement of graphene FET conductance when the solution in microfluidic channel was changed from pH 7.64 buffer to pH 6.91 buffer during a time period of 2 minutes. It was clearly observed that the FET conductance evolves from a plateau at 0.20 mS to another plateau at 0.22 mS during the time frame. This experiment further demonstrated that the graphene FET is capable of monitoring the pH change in microfluidic channels in real time.

Several examples of single layer, large area graphene electrodes as a platform for optical and biosensing devices were demonstrated. Graphene can be readily modified using various polymer films deposited through electrochemical methods. These electropolymerization processes significantly improve the prospects for using graphene in applications such as those that require a transparent electrode with electropolymerized materials. Simple modification of graphene with polymers can readily be used to improve its pH sensing properties and catalysis of biologically-relevant reactions. A working microfluidic device based on electrochemical gating of field effect transistors that is more responsive to pH changes than those reported was demonstrated.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A structure comprising:
   a) a transparent conducting substrate comprising a first graphene layer disposed on substantially all of a surface of a substrate; and
   b) a first electropolymerized polymer layer disposed on substantially all of the first graphene layer;
   wherein the structure has a first color or is colorless, and the first color is blue.

2. The structure of claim 1, wherein the transparent conducting substrate is a flexible substrate.

3. The structure of claim 2, wherein the flexible substrate comprises poly(ethylene terephthalate) (PET), poly-3,4-ethylenedioxythiophene-polystyrenesulfonate, polyethylene, polypropylene, or polystyrene.

4. The structure of claim 1, further comprising a first electrolyte layer disposed on at least a portion of the first electropolymerized conducting polymer layer.

5. The structure of claim 4, further comprising a second graphene layer disposed on at least a portion of the first electrolyte layer.

6. The structure of claim 5, wherein a flexible transparent polymer layer is disposed on at least a portion of the second graphene layer.

7. The structure of claim 5, wherein the second graphene layer is disposed on a flexible substrate.

8. The structure of claim 1, wherein the electropolymerized layer is a polythiophene, polythiophene derivative, polypyrrole, polypyrole derivatives, polyfuran, polyfuran derivatives, polyaniline, polyaniline derivative, polyphenylenediamine, polyphenylenediamine derivative, or a copolymer thereof.

9. The structure of claim 1, wherein the electropolymerized layer is a polymer of an organometallic compound, a coordination compound, or a copolymer thereof.

10. A method of forming a structure of claim 1 comprising:
    contacting a graphene layer disposed on substantially all of a surface of a substrate with a monomer under anodic or cathodic electropolymerization conditions such that an electropolymerized layer is formed on at least a portion of the graphene layer.

11. The method of claim 10, wherein the monomer is selected from the group consisting of:
    3,4-(1-thiomethyl)ethylenedioxythiophene; N-methoxyphenylpyrrole (e.g., 1-(4-methoxyphenyl)-pyrrole; N-phenylpyrrole; 3,4-ethylenedioxyselenophene; 3,4-propylenedioxypyrrole; 3,4-ethylenedioxypyrrole; 3,4-dimethoxypyrrole; N-methylpyrrole; pyrrole; 3,4-propylenedioxythiophene; poly(3,4-ethylenedioxythiophene (EDOT); 3,4-dimethoxythiophene; 3-methylthiophene; thiophene; [tris-(4-vinyl-4'-methyl-2,2'-bipyridine)M]$^{2+}$, where M is ruthenium, osmium, iron, cobalt, nickel, or rhenium, and combinations thereof.

12. The method of claim 10, wherein the anodic or cathodic electropolymerization conditions comprise cycling between a first potential and a second potential two or more times at a constant or varying current or cycling between a first current and second current at a constant potential.

13. A device comprising the structure of claim 1.

14. The device of claim 13, wherein the device is an electrochromic device, electrical-energy storage device, photo-voltaic device, field-effect transistor device, electrical device, electronic device, or energy-generation device.

15. The device of claim 14, wherein the device is an electrochromic device and the conducting substrate is glass.

16. The device of claim 15, wherein the conducting substrate is transparent and the electropolymerized layer is transparent or the electropolymerized layers are transparent.

17. The device of claim 14, wherein the device is a display, flexible display, light-emitting diode, sensor, battery, flexible battery, capacitor, flexible capacitor, supercapacitor or flexible capacitor.

18. The device of claim 13, wherein the device is a microfluidic device.

19. The structure of claim 1, wherein the substrate reversibly changes from colorless to a second color or changes from the first color to a second color via applying a potential to the substrate.

20. The structure of claim 19, wherein the second color is chosen from blue, red, orange, and green.

21. A structure comprising:
a) a transparent conducting substrate comprising a first graphene layer disposed on substantially all of a surface of a substrate; and
b) a first electropolymerized polymer layer disposed on substantially all of the first graphene layer,
wherein the structure has a first color or is colorless when a first potential is applied and has a second color or is colorless when a second potential is applied.

22. The structure of claim 21, wherein the first and/or second color is chosen from blue, red, orange, and green.

* * * * *